US012285192B2

(12) United States Patent
Dong et al.

(10) Patent No.: US 12,285,192 B2
(45) Date of Patent: Apr. 29, 2025

(54) PEDICLE SCREW-ROD SYSTEM CAPABLE OF GRADUALLY CHANGING FROM RIGID FIXATION TO NON-RIGID FIXATION

(71) Applicant: Jiangxi Provincial People's Hospital, Nanchang (CN)

(72) Inventors: Xieping Dong, Nanchang (CN); Qingli Li, Nanchang (CN); Weiyi He, Guangzhou (CN)

(73) Assignee: Jiangxi Provincial People's Hospital, Nanchang (CN)

( * ) Notice: Subject to any disclaimer, the term of this patent is extended or adjusted under 35 U.S.C. 154(b) by 515 days.

(21) Appl. No.: 17/638,116

(22) PCT Filed: Apr. 3, 2020

(86) PCT No.: PCT/CN2020/083228
§ 371 (c)(1),
(2) Date: Feb. 24, 2022

(87) PCT Pub. No.: WO2021/196163
PCT Pub. Date: Oct. 7, 2021

(65) Prior Publication Data
US 2022/0287740 A1    Sep. 15, 2022

(51) Int. Cl.
*A61B 17/70* (2006.01)
*A61B 17/00* (2006.01)
*A61B 17/86* (2006.01)

(52) U.S. Cl.
CPC ...... *A61B 17/7028* (2013.01); *A61B 17/7034* (2013.01); *A61B 17/7041* (2013.01); *A61B 17/8685* (2013.01); *A61B 2017/00004* (2013.01)

(58) Field of Classification Search
CPC ............ A61B 17/7028; A61B 17/7034; A61B 17/7041; A61B 17/8685; A61B 2017/00004
(Continued)

(56) References Cited

U.S. PATENT DOCUMENTS

2005/0085812 A1    4/2005   Sherman et al.
2011/0307016 A1   12/2011   Reglos et al.
(Continued)

FOREIGN PATENT DOCUMENTS

CN        1917909 A      2/2007
CN      203677226 U      7/2014
(Continued)

OTHER PUBLICATIONS

International Search Report and Written Opinion from International Application No. PCT/CN2020/083228 mailed Dec. 31, 2020.

*Primary Examiner* — Ellen C Hammond
*Assistant Examiner* — Tara Rose E Carter
(74) *Attorney, Agent, or Firm* — Hemisphere Law, PLLC; Zhigang Ma

(57) ABSTRACT

A pedicle screw-rod system capable of gradually changing from rigid fixation to non-rigid fixation is provided. The system includes a pedicle screw, a connecting rod, and a screw plug. The connecting rod is used for connecting in series the pedicle screw fixed to adjacent vertebrae on the same side of a spine, and the screw plug is used for locking the connecting rod on the pedicle screw intersecting therewith. At least one of two structural members of the pedicle screw or the connecting rod is connected by a flexible connecting part, and the flexible connecting part is also connected to degradable stoppers for preventing flexible parts from swinging with each other; and with gradual degradation of the degradable stoppers, a fixation manner of (Continued)

the pedicle screw-rod system will be gradually converted from initial rigid fixation into non-rigid fixation.

27 Claims, 14 Drawing Sheets

(58) Field of Classification Search
USPC .................................................. 606/250–279
See application file for complete search history.

(56) References Cited

U.S. PATENT DOCUMENTS

| | | | |
|---|---|---|---|
| 2021/0022726 A1* | 1/2021 | Bariteau | A61F 2/0811 |
| 2021/0177466 A1* | 6/2021 | Verlaan | A61L 27/222 |

FOREIGN PATENT DOCUMENTS

| | | |
|---|---|---|
| CN | 205411284 U | 8/2016 |
| CN | 108186093 A | 6/2018 |
| CN | 108186095 A | 6/2018 |
| CN | 108577954 A | 9/2018 |
| CN | 110141344 A | 8/2019 |
| CN | 110251220 A | 9/2019 |
| CN | 110478019 A | 11/2019 |

* cited by examiner

PEDICLE SCREW-ROD SYSTEM CAPABLE OF GRADUALLY CHANGING FROM RIGID FIXATION TO NON-RIGID FIXATION

TECHNICAL FIELD

The present disclosure relates to the technical field of medical apparatuses and instruments, and in particular, to a pedicle screw-rod system capable of gradually changing from rigid fixation to non-rigid fixation.

BACKGROUND ART

At present, pedicle screw-rod fixation systems used in the field of orthopedics and neurosurgery are mainly divided into two categories: one is a static type pedicle screw which enables a fixed segment to lose any activity, called "a static screw" for short, and the fixation is called rigid fixation; and the other is a dynamic type pedicle screw which enables the fixed segment to perform appropriate flexion-extension activities, called "a dynamic screw" for short, and the fixation is non-rigid fixation. Rigid fixation is relatively strong, which is conducive to fracture healing and intervertebral bony fusion. However, since the fixation is too strong, stress shielding can occur in the fixed segment, which results in disuse osteoporosis of a spine. Furthermore, over reliance on long-term protection of an internal fixture will lead to protection failure phenomena, such as fatigue fracture or loosening, of the internal fixture. Once an osteoporotic spine loses effective support of the pedicle screw that the spine relies on, it is more prone to injuries, such as osteoporotic fractures. Therefore, it is often necessary to designedly surgically take out the internal fixture after bone healing.

In addition, some injuries need to use the pedicle screw-rod system to support the spine in the early stage of a surgery to reduce the pressure on a vertebral body and an intervertebral body. With the healing of an incision and the enhancement of spinal stability, it is also hoped that the fixed segment has certain flexion-extension activities, that is, it is hoped to reduce the fixation strength of the pedicle screw-rod system and prevent the degeneration caused by stress concentration of adjacent segments.

In order to prevent the degeneration of the adjacent segments, non-rigidly fixed dynamic screw emerges as the times require. Since most of the pedicle screws are not fixed in situ, during an operation, after all pedicle screws are implanted and connecting rods are installed, screw seats of the pedicle screws are often opened or clamped by an expander or a clamp first, and drives screw bodies rigidly connected to the screw seats to lift the vertebral bodies fixed by the pedicle screws, so that all screw plugs are screwed to maintain the position and maintain the stability of the spine at the fixed segment after the adjacent vertebral bodies and intervertebral spaces are opened or closed to required positions. However, a dynamic screw with a screw body in a hinged state with the screw seat is affected by the resistance of soft tissues, such as an intervertebral disc and a ligament, since expanding and pressurizing tools only act on the screw seat, so that a front end of the screw body cannot move synchronously in parallel with the screw seat, but stays in place temporarily. Therefore, a coaxial relationship between the screw seat and the screw body is destroyed, and an included angle appears. Only when an opening or clamping force applied by a tool continues to act to enable a swinging included angle between the axis of the screw body and the axis of the screw seat to reach a design limit value, a lower part of the screw body can lift a front edge of the vertebral body to move, thereby achieving an opening or clamping effect. Thus, the swinging angle set by the dynamic screw will lose completely, and a flexion or extension movement manner in a flexion-extension function loses, so that an extension or flexion amplitude in an opposite direction is doubled, that is, the fixed segment can only swing 0 to 2 times a design angle (0 to 2*□). Both results of excessive or insufficient movement amplitude violate the original design intention of the dynamic screw, and may have an adverse impact on a human body, which cannot reflect the advantageous performance of the "dynamic screw", thereby seriously affecting the practical application of the advanced concept of dynamic fixation.

The screw body and the screw seat cannot move synchronously in the same direction in real time, which will inevitably and gradually lead to the tendency of forward angulation consistent with the screw body while adjacent vertebrae are opened along with the screw seat departing gradually, resulting in anterior flexion fixation. The tendency of backward angulation consistent with the screw body appears gradually while the adjacent vertebrae are compressed along with the screw seat getting close gradually, resulting in posterior extension fixation.

However, at present, there is no dynamic screw that can temporarily limit the dynamically connected screw body and screw seat to be relatively fixed in the direction of opening or pressurizing for facilitate operation during a surgery, and there is no pedicle screw-rod fixation system that can provide strong rigid fixation in an early stage of fixation and then is automatically converted into non-rigid fixation with relatively weak fixation strength.

In addition, due to the variety of injuries and diseases, it is difficult to determine which type of pedicle screw needs to be used before a surgery sometimes, even a surgical plan defined before a surgery may be modified due to intraoperative findings, so the dynamic screw or the static screw prepared before the surgery may not be suitable for further use. Therefore, it is necessary to prepare a whole set of static screw or dynamic screw and surgical tools thereof as backup before the surgery, which will invisibly increase the investment and consumption in human, financial, and material resources of sales enterprises and hospitals. Sometimes, in order to reduce consumption, in view of the above-mentioned rare cases, some surgeries in some hospitals will not make a backup. Once the backup is needed during the surgery, it is inevitable to pay the price of sacrificing the quality of medical care, such as sacrificing the fixation quality, increasing the intraoperative waiting time for instruments, prolonging the overall operation time, or the like. At this time, the pedicle screws that can consider both dynamic and static and convert between static and dynamic to meet the requirements of "one screw for three purposes" can be used as emergency backup mutually to solve urgent clinical problems.

Furthermore, the lower the height of the pedicle screw exposed outside a bone, that is, the lower the "notch", the less adverse stimulation to the human body. The vast majority of existing pedicle screws are of a "centrally located type" in which a connecting rod is directly squeezed by a screw plug to be closely connected with the screw seat and screw body as a whole. Therefore, the notch heightened by superimposing the connecting rod to the axis of the screw plug cannot be lowered, and the structure that a side wall of the screw seat is divided into two pieces by a U-shaped groove, of the "centrally located type" pedicle screw, for the connecting rod to clamp is also a weak point of the pedicle screw. When the screw plug is screwed too tightly, the side wall of the screw seat is expanded outward to cause a "thread disengagement" phenomenon that results in the loosening of the screw plug. Therefore, the disclosure with the application No. 201910494053.6 entitled with "anti-thread disengagement pedicle screw with external spring" proposes a "side mounted" pedicle screw with a screw plug and a connecting rod arranged in parallel, which can greatly lower the "notch" and completely solve the problem of "thread disengagement". However, there is no screwdriver interface at an upper end of the screw seat, so it is difficult to implant a screw. In addition, an arc surface for connecting the connecting rod is formed in only one side of the screw seat, and it is difficult to rotate the screw seat to an appropriate position during operation, so it is difficult to install.

Based on the abovementioned actual situations, a pedicle screw-rod system capable of gradually changing from rigid fixation to non-rigid fixation is provided.

SUMMARY

In view of the above-mentioned difficult problems that need to be solved urgently clinically, the present disclosure applies for and discloses a pedicle screw-rod system capable of gradually changing from rigid fixation to non-rigid fixation by using the characteristics of biomaterials, such as metal magnesium, a magnesium alloy, a magnesium-polylactic acid composite, and zinc, with certain stiffness and hardness and can be degraded and absorbed in vivo. The pedicle screw-rod system capable of gradually changing from rigid fixation to non-rigid fixation includes a pedicle screw, a connecting rod, and a screw plug. The connecting rod is used for connecting in series the pedicle screw fixed to adjacent vertebrae on the same side of a spine, and the screw plug is used for locking the connecting rod on the pedicle screw intersecting therewith. At least one of two structural members of the pedicle screw or the connecting rod is connected by a flexible connecting part, and the flexible connecting part is also connected to a degradable stopper for preventing flexible parts from swinging each other. With gradual degradation of the degradable stopper, a fixation manner of the pedicle screw-rod system will be gradually converted from initial rigid fixation into non-rigid fixation.

In one embodiment, the flexible connecting part includes a spring. One end of the spring is connected to a screw seat, and the other end of the spring is connected to a screw body.

In one embodiment, external threads matched with threads in an inner wall of the spring in shape are formed in an outer surface of the degradable stopper. A first screwdriver interface is formed in the center of an upper end face of the degradable stopper. A bulge matched with a blind hole in an upper end of the screw body is formed in the center of a lower end of the degradable stopper in the axial direction.

In one embodiment, the screw seat is of a cylinder structure with a thin upper part and a thick lower part, a high upper part and a low lower part, and a circular arc surface transition. The radian radius of the circular arc surface of an outer edge of the screw seat is consistent with the radius of the connecting rod.

A second screwdriver interface is formed in an upper end face of the screw seat. The second screwdriver interface includes notches that are symmetrically formed in a peripheral wall of the screw seat about an axis.

In one embodiment, the pedicle screw-rod system capable of gradually changing from rigid fixation to non-rigid fixation further includes a hook frame used for fastening the connecting rod. The hook frame includes a lantern ring and a barb-shaped rod pressing arm which is arranged on a side of the lantern ring and extends outwards. The lantern ring is connected to an outer edge of the screw seat in a sleeving manner. A lower edge of the rod pressing arm is a rod pressing arc surface with the radius consistent with that of the connecting rod.

After the hook frame is connected to the screw seat in a sleeving manner. A semicircular arc surface of the rod pressing frame and a circular arc transition surface of the outer edge of the screw seat form a tunnel for accommodating the connecting rod together, so that the connecting rod is located on the outer side of the screw seat.

In one embodiment, the connecting rod includes one section or a plurality of sections of flexible bodies that are distributed at intervals, rigid rods connected to two ends of the flexible bodies, and degradable stoppers bridged on the rigid rods at two ends of the flexible section to limit the bending of the flexible section. The degradable stoppers may be gradually degraded, softened, and thinned in a human body until disappearing, and the connecting rod will gradually obtain the preset flexibility.

In one embodiment, the flexible body includes a cylindrical spring. The outside diameter of the cylindrical spring is less than or equal to that of the rigid rods.

In one embodiment, the degradable stoppers are of tubular structures, and are connected to the flexible section of the connecting rod and the peripheries of the adjacent rigid rods at both ends thereof in a sleeving manner in a rigid state.

In one embodiment, the degradable stoppers are of inner core structures, and cylindrical springs extend out from both ends after the degradable stoppers are inserted or screwed into the cylindrical springs. Blind holes matched with the cylindrical springs extended out from the degradable stoppers are also formed in end faces of the rigid rods in the axial direction.

In one embodiment, the degradable stoppers may be manufactured by a degradable biomaterial, and is made of a magnesium metal/polylactic acid composite material which takes a magnesium metal with higher elastic modulus and higher degradation rate as an inner core and takes polylactic acid with lower elastic modulus and lower degradation rate as a surface layer.

In one embodiment, there is no screw head at the upper end of the screw body. The upper end face is a plane. A circular blind hole is formed in the center of the upper end face in the axial direction. An adaptation groove matched with the lower end of the spring in shape is also formed in the edge of the upper end face of the screw body.

In one embodiment, an upper end of the spring is screwed with an internal threaded through hole that is axially formed in the lower end of the screw seat and is permanently and mechanically fixed. A lower end of the spring is permanently and mechanically fixed after being adaptively connected to the adaptation groove in the upper end of the screw body.

In one embodiment, the screw body, the screw seat, the spring connected therebetween, the flexible bodies and the rigid rods in the connecting rod, and the connection between the flexible bodies and the rigid rods are all integrally manufactured in an additive manufacturing manner.

In one embodiment, a lantern ring inner cavity of the hook frame is matched with an outer edge of the screw seat. The lantern ring and the rod pressing arm are of an integrated structure. The rod pressing arc surface intersects with the lantern ring inner cavity, so as to from a lantern ring gap.

In one embodiment, the screw plug includes an upper cover. A third screwdriver interface is formed in the center of the upper cover. External threads matched with the internal threads at the upper end of the screw seat are formed in a lower part of the screw plug.

In one embodiment, an end face of the rigid rod is provided with a concave structure or a screw core-shaped structure matched with an outer surface of the cylindrical spring. The cylindrical spring is fixedly connected to the rigid rod through the concave structure or the screw core-shaped structure.

In one embodiment, external threads matched with the inner cavity of the cylindrical spring are formed in the middle section of the degradable stopper, and external threads matched with threaded blind holes in the end faces of the rigid rod are formed in both ends.

In one embodiment, a sphere head is arranged at the upper end of the screw body. The sphere head at the upper end of the screw body may also be hinged to the lower end of the screw seat in a clearance fit state. The screw body and the screw seat can swing and rotate under the action of an external force.

In one embodiment, after the screw plug is fastened, the connection between the screw body and the screw seat may also be converted into rigid connection by making a fitting pair consisting of the connecting rod, the degradable stopper, the sphere head of the screw body, and the lower end of the screw seat in interference fit. As the degradable stopper is gradually degraded, thinned, and softened until it disappears, the original clearance fit of the fitting pair consisting of the connecting rod, the sphere head of the screw body, and the lower end of the screw seat gradually recovers.

In one embodiment, the upper end of the screw seat is provided with a U-shaped groove and is provided with internal threads matched with the screw plug. The whole body, except the two ends, of the connecting rod is cylindrical. Before the degradable stopper is added, the highest point of a top end of the sphere head is not higher than the plane of a connecting line of bottoms of the U-shaped grooves on both sides.

In one embodiment, when the screw body is coaxially installed into the screw seat, the upper end face of the degradable stopper is a plane perpendicular to an axis of the screw body-screw seat or a concave arc surface that is provided with an axis perpendicular to the screw body-screw seat and is in arc surface contact with the lower edge of the connecting rod.

In one embodiment, the sphere head of the upper end of the screw body is a semi-sphere with a concave type screwdriver interface in a top end, or a sphere with a convex screwdriver interface in the top end. After the degradable stopper is added to the upper end of the sphere head of the screw body, the lower edge of the connecting rod and the upper end face of the stopper have a structural feature that is in linear or line-shaped arc surface contact in the axial direction of the connecting rod.

In one embodiment, after the degradable stopper is added on the upper end of the sphere head of the screw body, a natural state is that the upper end face, compressed by the connecting rod, of the degradable stopper is higher than the plane of the bottom of the U-shaped groove of the screw seat. At this moment, the connecting rod clamped into the U-shaped groove of the screw seat cannot be in contact with the bottom of the U-shaped groove naturally. The surface of the stopper may be compressed to sink by the connecting rod, so as to be closely connected to the bottom of the U-shaped groove.

In one embodiment, the sphere head of the upper end of the screw body is a regular semi-sphere with a concave type screwdriver interface in the top end. A side wall of the screwdriver interface forms a circle of platform at the top end of the sphere head. The degradable stopper is provided with a through hole for a screwdriver to penetrate through along the axis. The lower end face of the degradable stopper is in a plane shape adapted to the platform.

In one embodiment, the sphere head of the upper end of the screw body is a high semi-sphere with a concave type screwdriver interface in the top end. The side wall of the screwdriver interface forms a circle of platform with the outside diameter less than the sphere diameter at the top end of the sphere head. The degradable stopper is provided with a through hole for a screwdriver to penetrate through along the axis. The lower end face of the degradable stopper is a plane that is matched with the top end of the high semi-spherical sphere head and extends from the concave spherical surface of an outer ring and the platform of an inner ring.

In one embodiment, the sphere head of the upper end of the screw body is a high semi-sphere with a concave type screwdriver interface in the top end. An outer edge of the top end of the sphere head is connected with a non-degradable pressing ring with a plane serving as an upper surface and a concave spherical surface serving as a lower surface. The degradable stopper is provided with a through hole for the screwdriver to penetrate through along the axis. The degradable stopper is tiled on the pressing ring.

In one embodiment, the screwdriver interface at the top end of the sphere head of the screw body is a convex type with a hexagonal or quadrangular or elliptical cylindrical cross section. A boss containing the axis of the screw body is processed at the upper end of the convex type screwdriver interface. The spherical shape of the top end of the boss is kept as same spherical surface of the sphere head of the screw body with an overlapped sphere center. The degradable stopper is wrapped and attached to the outer edge of the boss, but does not cover the spherical surface of the top end of the boss. The spherical surface of the top end of the boss is not higher than the bottom surface of the U-shaped groove of the screw seat. The outside diameter of the degradable stopper is not greater than the minimum diameter of the screwdriver interface.

The pedicle screw-rod system capable of gradually changing from rigid fixation to non-rigid fixation provided by the present disclosure can achieve the objectives of "preventing thread disengagement" and "low notch". An inner core type stopper manufactured by a degradable hard biomaterial serves as a movement limiting device of a dynamic pedicle screw. Firstly, the operations of implanting in vivo and opening or compressing are facilitated. Secondly, strong static fixation in an initial stage of fixation is realized. Thirdly, the pedicle screw can be gradually converted into dynamic fixation that allows the fixed segment to move moderately in a process that the movement limiting device is degraded gradually. The pedicle screw is in a neutral position state when it is implanted and after it is opened or pressurized. Therefore, after the movement limiting device is degraded, the pedicle screw has activity in both flexion and extension directions, so that a dynamic fixation effect of the dynamic pedicle screw-rod system can be ensured to the greatest extent. Moreover, according to specific conditions in the surgery, the pedicle screw-rod system can temporarily decide to adopt which of three fixation manners of permanent and rigid fixation, permanent and non-rigid fixation, and first rigid fixation and then non-rigid fixation only by selecting the material of the stopper and selecting whether to install it or not. That is, if the stopper made of a non-degradable material is installed, an effect of permanent and rigid fixation will be achieved; if the stopper is not installed, an effect of permanent and non-rigid fixation will be achieved; and if the stopper made of a degradable material is used, then an effect of first rigid fixation and then non-rigid fixation will be achieved. Therefore, the present disclosure can also achieve the multi-purpose of "one screw for three purposes".

BRIEF DESCRIPTION OF THE DRAWINGS

To describe the technical solutions in the embodiments of the present disclosure more clearly, the following briefly describes the accompanying drawings required for describing the embodiments. Apparently, the accompanying drawings in the following descriptions show merely some embodiments of the present disclosure, and a person of ordinary skill in the art may derive other drawings from these accompanying drawings without creative efforts.

DETAILED DESCRIPTION OF THE EMBODIMENTS

Figure 1:
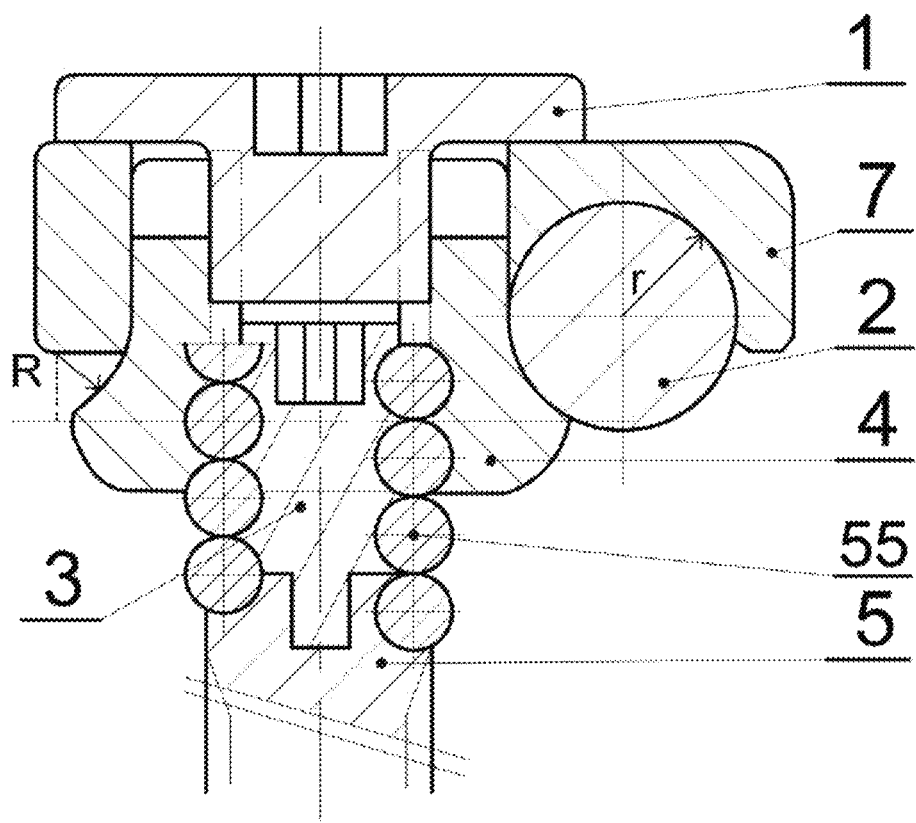
FIG. 1 is a structural schematic diagram of Embodiment 1 of the present disclosure.

Technical solutions in the embodiments of the present disclosure will be clearly and completely described herein below with reference to the drawings in the embodiments of the present disclosure. Apparently, the described embodiments are merely part rather than all of the embodiments of the present disclosure. On the basis of the embodiments of the present disclosure, all other embodiments obtained by those of ordinary skill in the art without creative work fall within the scope of protection of the present disclosure.

Embodiment 1 provides a pedicle screw-rod system capable of gradually changing from rigid fixation to non-rigid fixation. The pedicle screw-rod system consists of a pedicle screw consisting of a screw seat and a screw body, and a matched hook frame, a connecting rod, a screw plug, and a degradable stopper. A lower end of the screw seat 4 is connected to an upper end of the screw body 5 through a cylindrical spring 55. The screw seat 4 is shaped like a hollow circular nut, and the appearance thereof has a thin upper part and a thick lower part, a high upper part and a low lower part, and a circular arc surface transition. The circular arc surface transition is also a screw seat rod holding arc surface 48, and the radian radius R thereof is consistent with the radius r of the connecting rod 2. Internal threads matched with the screw plug 1 are formed in an opening in an upper part of an inner cavity of the screw seat, and an internal threaded through hole 49 that is matched with the outer part of the cylindrical spring 55 in size and shape is axially formed in the lower part of the inner cavity. A second screwdriver interface 46 is formed in an upper end face of the screw seat 4, and the second screwdriver interface 46 includes notches that are symmetrically formed in a peripheral wall of the screw seat about an axis, preferably, two pairs of crossed notches.

The screw body 5 is a cylindrical or conical screw screwed into a spine. There is no screw head at the upper end of the screw body. The upper end face is a plane. A circular blind hole 56 is formed in the center of the upper end face in the axial direction. The blind hole 56 may be cylindrical, conical, or frustum cone-shaped. An adaptation groove 57 matched with the lower end of the spring 55 in shape is also formed in the edge of the upper end face of the screw body 5.

The spring 55 is a cylindrical spring with sufficient stiffness. An upper end of the spring is screwed with an internal threaded through hole 49 that is axially formed in the lower end of the screw seat and is permanently and mechanically fixed. The lower end of the spring 55 is permanently and mechanically fixed after being adaptively connected to the adaptation groove 57 in the upper end of the screw body.

Preferably, the screw seat, the screw body, and the spring connected therebetween are integrally formed and manufactured through 3D printing.

The hook frame 7 includes a lantern ring 71 that is connected to an outer edge of the screw seat 4 in a sleeving manner. A lantern ring inner cavity 711 is matched with the outer edge of the screw seat 4. One side of the lantern ring is provided with a barb-shaped rod pressing arm 73 that extends outwards. The lantern ring and the rod pressing arm 73 are of an integrated structure. A lower edge of the rod pressing arm is a rod pressing frame 75 formed with the nearly semicircular rod pressing arm 73 with consistent radius with the connecting rod 2. Preferably, the rod pressing arm 73 intersects with the lantern ring inner cavity 711 to form a lantern ring gap 712. After the hook frame 7 is connected to the screw seat 4 in a sleeving manner, a small semicircular arc surface of the rod pressing frame 75 and the screw seat rod holding arc surface 48 together form a tunnel that just contains the connecting rod 2. At this time, the connecting rod 2 is placed in the tunnel, and is screwed into the internal threads at the upper end of the screw seat 4 through the screw plug 1, so that the connecting rod 2 can be prevented from removing. The screw plug 1 is screwed, so that the connecting rod 2 can be forced to fasten the screw seat 4 through the lantern ring gap 712 while tightening the connecting rod 2.

The whole body, except the two ends, of the connecting rod 2 is cylindrical, and may be straight, or bent at a radian.

The screw plug 1 is provided with an upper cover 13. A third screwdriver interface 12 is formed in the center of the upper cover. A lower part of the screw plug 1 is external threads 11 matched with the internal threads 45 at the upper end of the screw seat.

Figure 5:
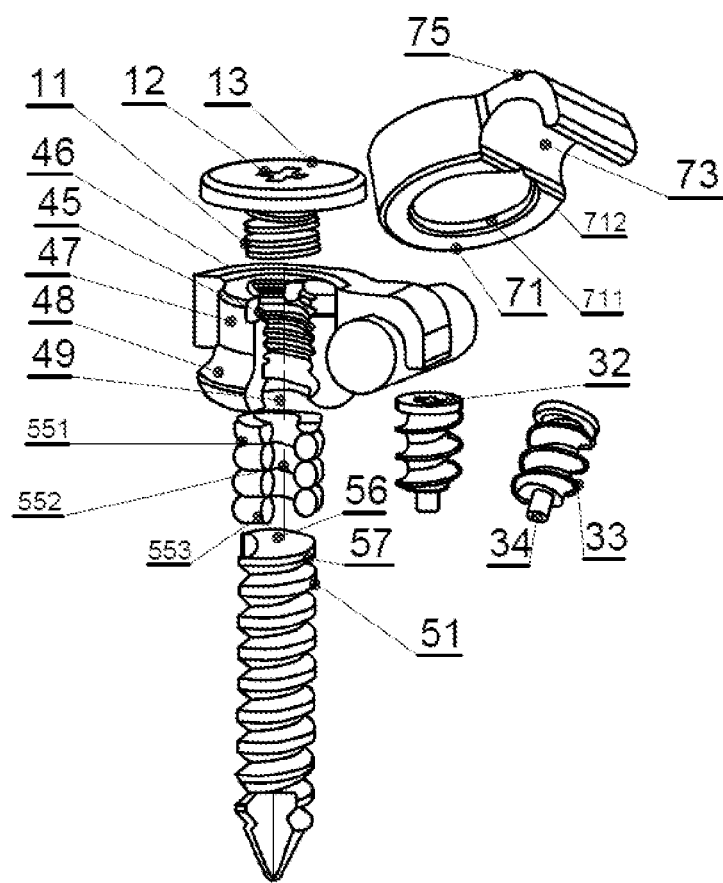
FIG. 5 is a structural decomposition schematic diagram of Embodiment 1 of the present disclosure.

The first degradable stopper 3 is a degradable inner core type stopper that can be screwed into an inner cavity of the spring 55. External threads 33 matched with the threads in the inner wall of the spring 55 in shape are formed in the outer surface of the degradable stopper 3. A screwdriver interface 32 is formed in the center of the upper end face of the first degradable stopper 3. A bulge 34 matched with a blind hole 56 at an upper end of the screw body is formed in the center of a lower end of the first degradable stopper 3 in the axial direction. The bulge 34 is cylindrical, conical, or frustum cone-shaped. The first degradable stopper 3 is preferably made of a magnesium metal/polylactic acid composite material which takes the magnesium metal with higher elastic modulus and higher degradation rate as an inner core and takes polylactic acid with lower elastic modulus and lower degradation rate as a surface layer. A structure, a combination, and functions of the present disclosure can be clearly shown in FIG. 1 and FIG. 5. FIG. 1 shows a two-dimensional drawing and an outline drawing of the present application. FIG. 5 is an exploded effect drawing of the present application. It can be seen from the above-mentioned two drawings that the pedicle screw of the present disclosure is formed by respectively connecting and permanently fixing an upper end 551 and a lower end 553 of the spring 55 to the screw seat 4 and the screw body 5. The axes of the three are overlapped. The screw body 5 and the screw seat 4 can swing to various directions by taking the spring 55 as a turning point. After the first degradable stopper 3 is screwed into a spring inner cavity 552, the bulge 34 at the lower end of the stopper is inserted into the blind hole 56 in the upper end of the screw body, so that the spring 55 is prevented from bending, and the pedicle screw is in rigid connection that the screw body 5 and the screw seat 4 are in a coaxial neutral state, thereby facilitating a screw implanting operation. During a surgery, after all pedicle screws are implanted into the spine, the connecting rod 2 is placed on one side of the screw seat 4 and the hook frame 7 is arranged in an outer cylindrical surface 47 of the screw seat. When the external threads 11 at the lower end of the screw plug 1 are screwed into the internal threads 45 of the screw seat, the connecting rod 2 is hooked by the hook frame 75 and is restrained on the screw seat 4. At this moment, the operation of opening or pressurizing the spine can be easily realized relying on the pedicle screw in rigid neutral position connection, and the angulation of a fixed segment cannot be caused by stressed angulation of the screw body 5 and the screw seat 4. After opening and supporting are completed, when the screw plug 1 is screwed, the connecting rod 2 will be locked by the rod pressing frame 75 of the hook frame 7 and the screw seat rod holding arc surface 48 together through downward pressure of the upper cover 13 of the screw plug.

Figure 2:
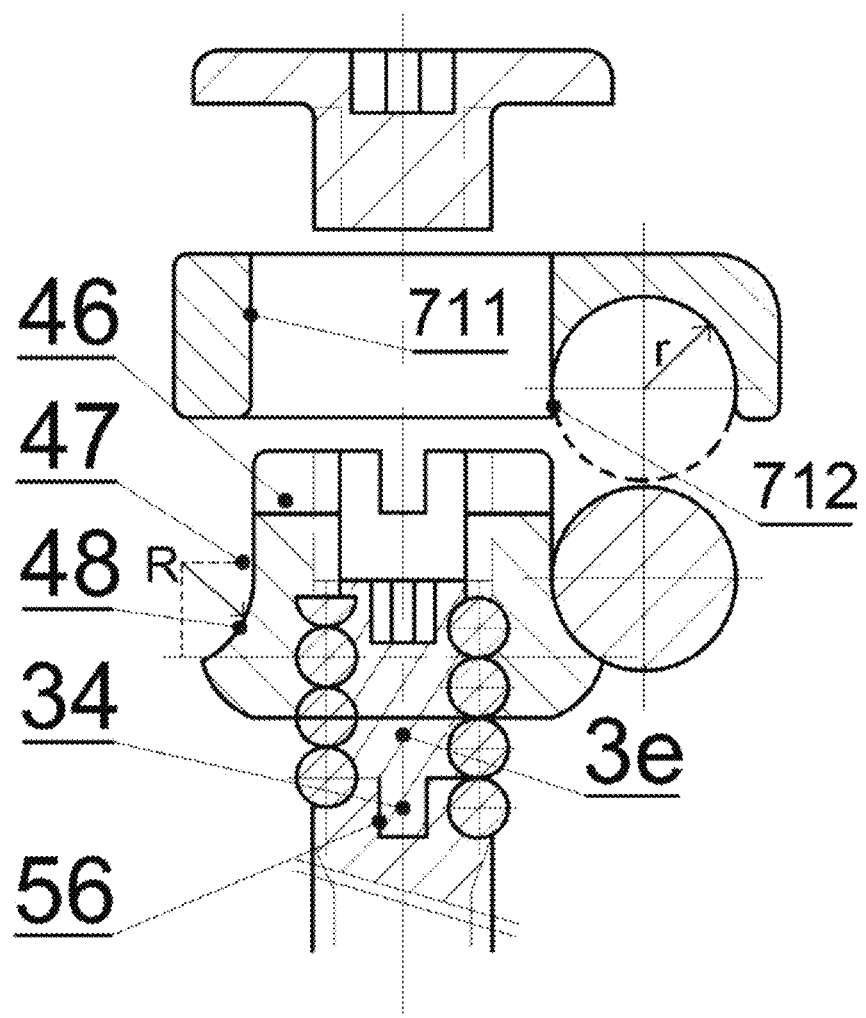
FIG. 2 is a schematic diagram of constraining a connecting rod by a screw seat and a hook frame jointly of the present disclosure.

FIG. 2 further illustrates structures and mutual relationships of relevant parts with the two-dimensional diagram of the assembly of the present disclosure. FIG. 2 clearly shows the shape of the second screwdriver interface 46 at the upper end of the screw seat. The pedicle screw may be screwed, by using the second screwdriver interface 46 at the upper end of the screw seat, into the spine when the inner core type stopper 3e is not added. The structure is an important optimization and improvement of the patent application with the application No. 201910494053.6.

Since the dynamic screw with the external spring is that a section of spring between the screw seat 4 and the screw body 5 can still bend to produce a function of "dynamic screw" by the spring 55 after connecting the screw seat 5 and the screw body 4, the overall pedicle screw can be "static" or "dynamic" by only controlling the activity of the section of spring. The inner core described in the present application realizes a multi-purpose clinical effect shown in the present application by using the characteristic.

Figure 3:
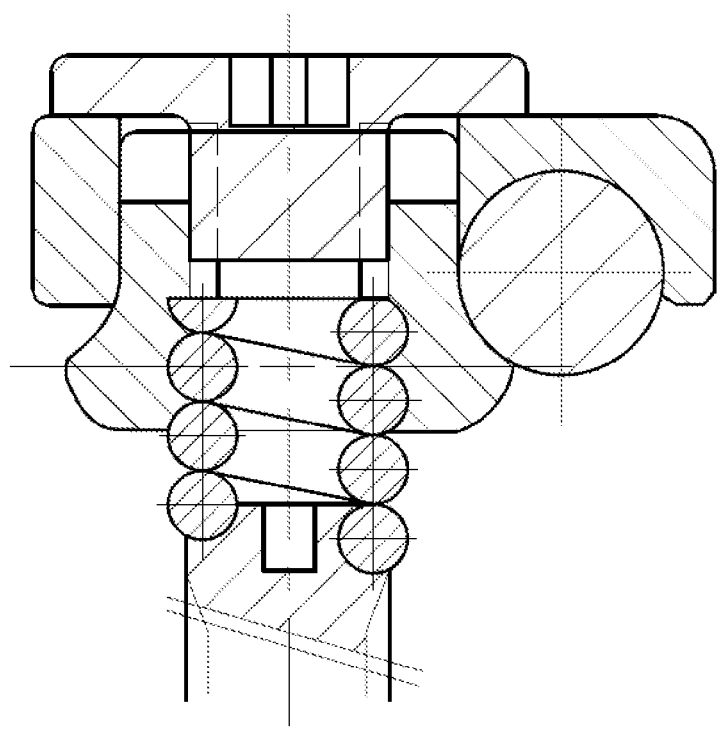
FIG. 3 is a schematic diagram of a "dynamic" purpose of the present disclosure.
Figure 4:
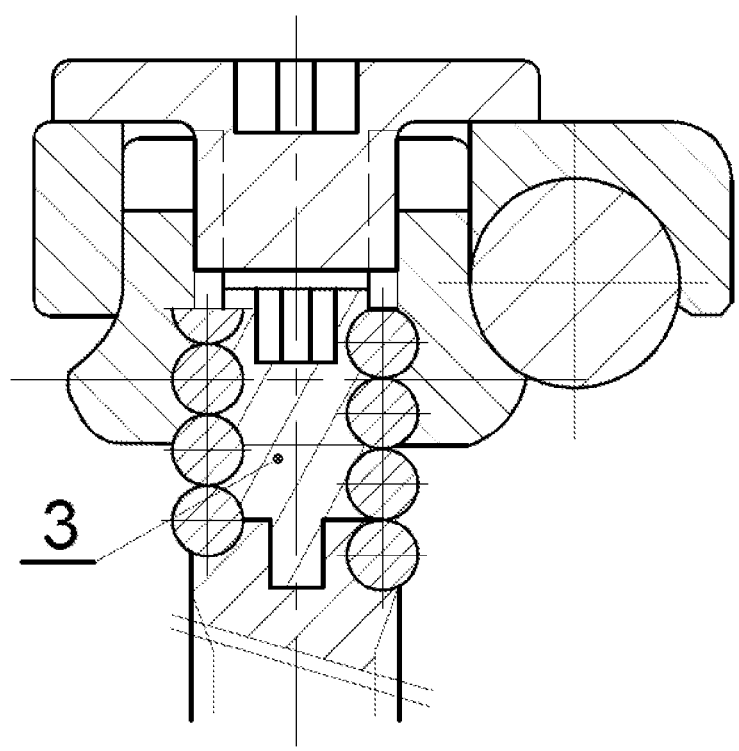
FIG. 4 is a schematic diagram of a "static" purpose of the present disclosure.

A structure and a limiting mechanism of the stopper are further described in the present disclosure with FIG. 3 and FIG. 4. As shown in FIG. 3, the first degradable stopper 3 is an inner core type stopper, the outer surface thereof is processed into a cylindrical body with threads 33 matched with the inner cavity 552 of the spring 55, an upper end face thereof is provided with a first screwdriver interface 32 for a screwdriver to act, and a lower end thereof is provided with a bulge 34. When the first degradable stopper 3 is not placed into the inner cavity 552 of the spring 55, the screw body 5 and a human body spine into which the screw body 5 is implanted may swing at a certain angel relative to the screw plug 1, the hook frame 7, the connecting rod 2, and the screw seat 4 that have been connected together. As shown in FIG. 3, the pedicle screw shown in the present application presents the function of "dynamic screw". When the first degradable stopper 3 is screwed into the inner cavity 552 of the spring 55 with the inner core external threads 33 on the outer surface thereof by using a screwdriver, the bulge at the lower end of the inner core type stopper is screwed into the matched blind hole 56 in the upper end of the screw body, so that the spring 55 cannot bend, and the screw seat 4 and the screw body 5 become coaxial, that is, the rigidity of the neutral state. The screw body 5 cannot swing relative to the screw seat 4, and the pedicle screw becomes a "static screw", as shown in FIG. 4. If the first degradable stopper 3 selects a non-degradable material, the first degradable stopper 3 will be clamped into the inner cavity 552 of the spring 55 all the time. The overall pedicle screw is presented as the "static screw" all the time. The inner core type stopper of the present disclosure is made of the degradable material, so that the pedicle screw will gradually change from the static screw that achieves an effect of rigid fixation in the initial fixation to the dynamic screw that achieves an effect of non-rigid fixation when the inner core type stopper is gradually degraded, thinned, softened, and finally absorbed as time goes on, that is, the combination as shown in FIG. 4 is returned to the combination shown in FIG. 3, so that the objective of the present disclosure of "presenting a fixed screw at the initial stage of a surgery, and then gradually switching to a dynamic screw" is achieved.

Figure 9:
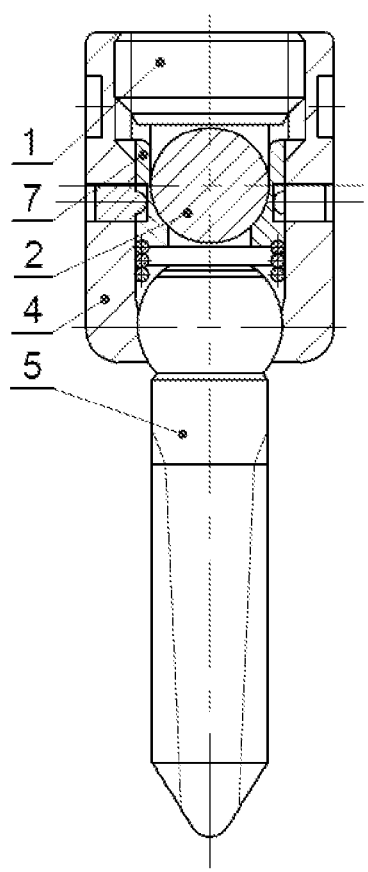
FIG. 9 is a structural schematic diagram of a centrally located dynamic screw of the existing connecting rod.

The pedicle screw disclosed in the present application adopts a structural form of a "side-mounted connecting rod type". The connecting rod 2 is moved to one side of the screw seat 4, so as to effectively reduce the height of a notch. FIG. 9 shows a currently popular "side-mounted connecting rod type" dynamic screw, which has the notch height of about 18 mm, while the height of the notch of the present application shown in FIG. 1 is only about 12 mm, and the reduced notch height reaches about 6 mm, so that adverse stimulation of an implant to paravertebral muscle can be greatly reduced, and a postoperative experience of a patient can be greatly improved.

From the effect drawing of a typical "centrally-mounted connecting rod type" pedicle screw in FIG. 9, it can be seen that when the connecting rod is downward compressed by the screw plug by using the internal threads on the screw seat, a lateral component force for opening the U-shaped opening through groove on the screw seat to both sides will inevitably be produced according to a working principle of the threads, so as to cause the loosening of the screw plug, and more seriously, lead to medical accidents of screw plug falling off and fixation failure. According to the multi-purpose pedicle screw as shown in the present application, the overall screw seat 4 is a circular tube almost without a weak point except that the upper end has a narrow and shallow second screwdriver interface 46 since the connecting rod 2 is mounted on a side, and the hook frame 7 connected to the outer cylindrical surface 47 of the screw seat in a surrounding and sleeving manner, so that the screw seat 4 cannot be opened on both sides no matter how much downward pressure is applied to the upper cover 13 of the screw plug. Therefore, an "anti-thread disengagement" clinical purpose is achieved.

Figure 10:
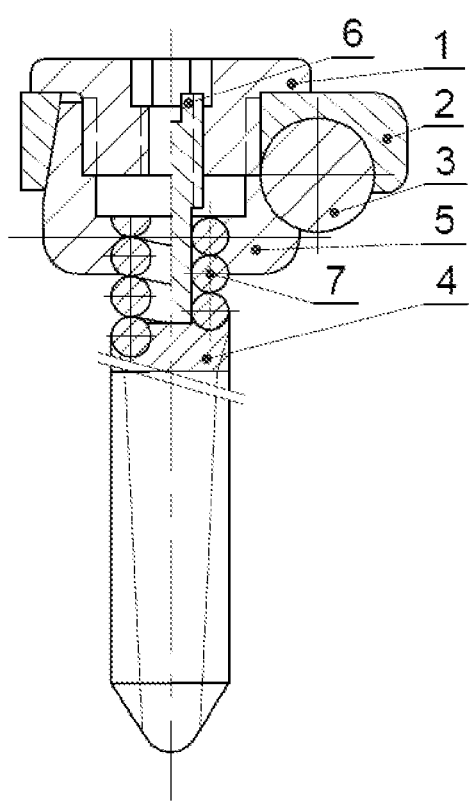
FIG. 10 is a structural schematic diagram of an anti-thread disengagement pedicle screw with an external spring.

FIG. 10 is an disclosure patent with the application No. 201910494053.6 entitled with "anti-thread disengagement pedicle screw with external spring". There is not screwdriver interface at an upper end thereof, so it is difficult to operate during screw implanting. In addition, an arc surface that can be used for the connecting rod to connect is formed in one side of the screw seat. During operation, it is difficult to screw the screw seat to a proper position, so it is difficult to install. On the contrary, in the present disclosure as shown in FIG. 2, the screw seat 4 has the second screwdriver interface 46 that facilitates screw implanting, and the outer edge of the overall screw seat is a circle of rod holding arc surface with a uniform shape, so that the pedicle screw can be installed smoothly no matter what angle the screw seat 4 is rotated.

Figure 6:
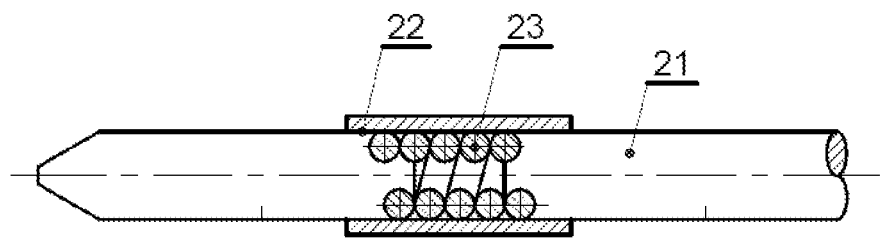
FIG. 6 is one structural schematic diagram of a connecting rod of the present disclosure.
Figure 8:
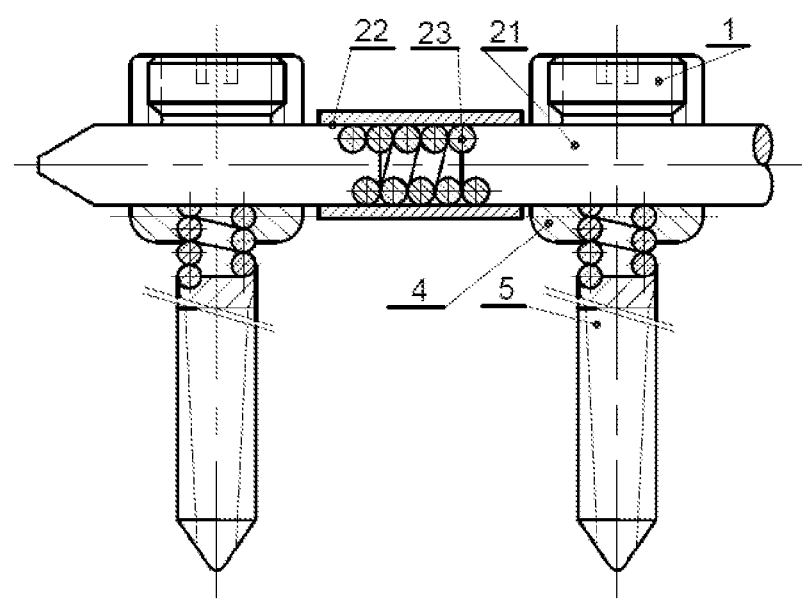
FIG. 8 is an installation diagram of the connecting rod of the present disclosure.

FIG. 6 and FIG. 8 are a connecting rod structural schematic diagram and a connecting rod installation schematic diagram of the present disclosure. The connecting rod includes one section or a plurality of sections of flexible bodies 23 that are distributed at intervals, rigid rods 21 connected to two ends of the flexible bodies 23, and second degradable stoppers 22 bridged on the rigid rods 21 at two ends of the flexible section to limit the bending of the flexible section. The second degradable stoppers 22 may be gradually degraded, softened, and thinned in a human body until it disappears, and the connecting rod will gradually obtain the preset flexibility.

The outside of the cylindrical spring 23 of an original spring rod is connected to a degradable tubular object in a sleeving manner. Since the outside diameter of the spring is not greater than those of rigid sections at both ends of the connecting rod, the inside diameter of the tubular object is not less than the outside diameters of the two ends of the connecting rod, (in fact, the spring and the connecting rod are set as micro-clearance fit). During surgery, the degradable tubular object is penetrated into the rod and is placed outside the spring. Since the tubular object is longer than a spring section, both ends of the tubular object must be overlapped at a connection between the rod and the spring to clamp the spring, so that the spring cannot bend. Therefore, the overall rod is of a rigid structure, but as time passes, the degradable material disappears, and the spring is out of restraint, and the rod can swing.

Figure 7:
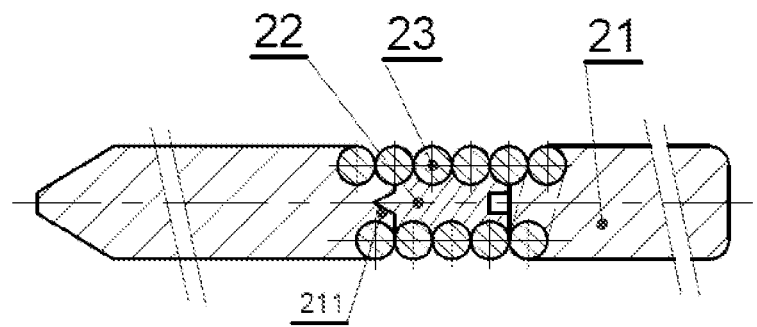
FIG. 7 is another structural schematic diagram of the connecting rod of the present disclosure.

Further, as shown in FIG. 7, the second degradable stopper 22 may also be of an inner core structure. That is, the second degradable stopper 22 is placed in the inner cavity of the cylindrical spring 23 and is bridged with the end faces of the rigid rods 21 on both ends. Preferably, a middle section of the second inner core type stopper 22 is in the shape of external threads matched with the inner cavity of the cylindrical spring 23, and both ends may be bulges extending out from the cylindrical spring 23, or may be blind holes formed in the axial direction. Correspondingly, an end face of the rigid rod 21 is provided with a bulge or a blind hole matched with the bulge or the blind hole of the cylindrical spring 23. Further, the connection 211 between the bulge and the blind hole may be realized through conical, frustum cone-shaped or cylindrical plugs that are matched with each other, and may also be in threaded connection. In order to ensure that the threaded bulge is consistent with the spring lead of the cylindrical spring 23, so as to realize close connection between the cylindrical spring 23 and the rigid rod 21 and mechanical connection, such as welding, in this state, the threads of the bulge and the blind hole are set as double threads or helix threads.

The stoppers made of a degradable biomaterial is made of a magnesium metal/polylactic acid composite material which takes a magnesium metal with higher elastic modulus and higher degradation rate as an inner core and polylactic acid with lower elastic modulus and lower degradation rate as a surface layer.

In addition, a hinge manner between the screw seat 4 and the screw body 5 is further described in the present disclosure with FIG. 11 to FIG. 18. The first degradable stopper includes a stopper 3a, a stopper 3b, a stopper 3c, and a stopper 3d.

Figure 11:
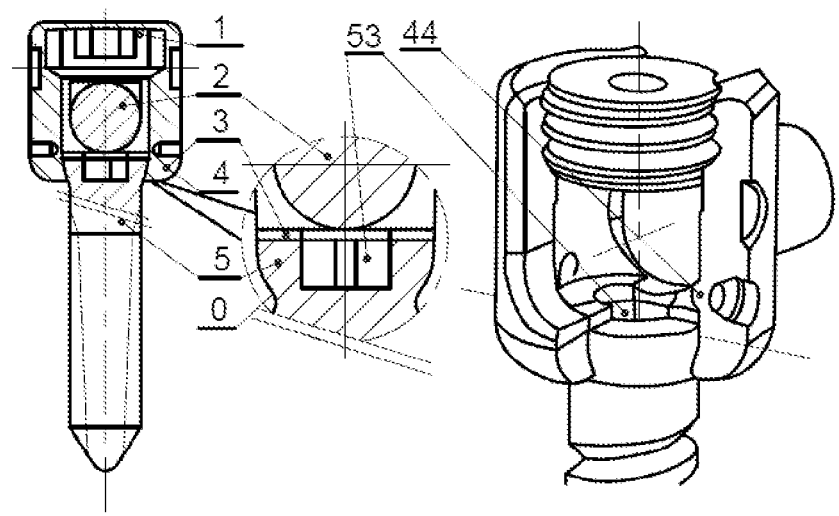
FIG. 11 is a two-dimensional diagram and an effect schematic diagram of Embodiment 2 of the present application.
Figure 12:
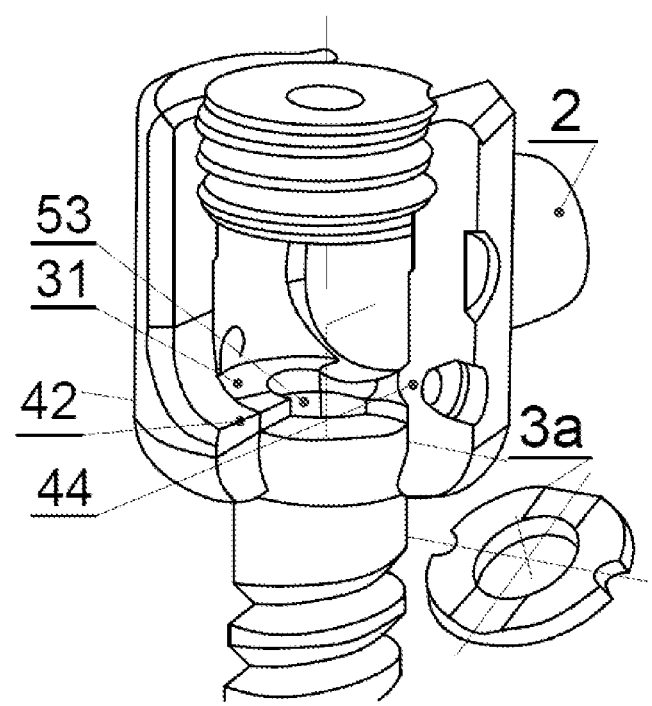
FIG. 12 is a schematic diagram of another implementation manner of a degradable stopper in Embodiment 2 of the present application.
Figure 18:
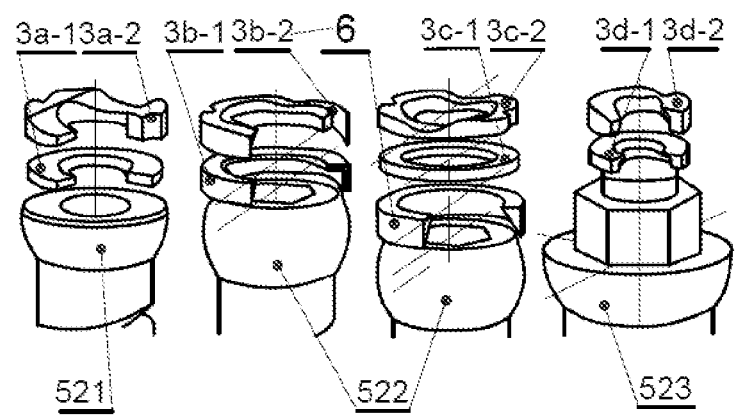
FIG. 18 is an effect schematic diagram of three types of bulbs and matched four types of limiters of the present application.

Embodiment 2, as shown in FIG. 11, FIG. 12, and FIG. 18, is a dynamic screw that a screw body sphere head 52 is hinged to an inner spherical surface 41 of a lower end of a screw seat through a ball-socket structure in a clearance fit state. The screw body sphere head 52 is a regular semi-spherical screw body sphere head 521 with a concave type screwdriver interface at a top end. A side wall of the screwdriver interface forms a circle of platform at the top end of the regular semi-spherical screw body sphere head 521. A degradable stopper 3a made of a hard biomaterial is added to the top end of the regular semi-spherical screw body sphere head 521. A lower end face of the degradable stopper 3a is in a plane shape adapted to the platform. According to the shape of an upper end face 31 of the degradable stopper 3a when the screw body 5 is installed into the screw seat 4 coaxial with the screw seat 4, the degradable stopper 3a is divided into a plane type 3a-1 perpendicular to the plane of the axis of the screw body-screw seat and a concave arc 3a-2 with a concave arc surface that is perpendicular to the axis of the screw body-screw seat and is in arc surface contact with a lower edge of a connecting rod 2. Further, the degradable stopper 3a is provided with a circular hole that is perpendicular to a cross section and may be used for a screwdriver to pass through to connect a screwdriver interface 53 of the sphere head of a screw body 5. The degradable stopper 3a may be assembled in the screw seat 4 before a surgery, and is blocked by an anti-falling bulge 44 of a retaining device, which does not falls off easily.

Preferably, in the present embodiment, before the degradable stopper 3a is not added, and after the connecting rod 2 is clamped into a U-shaped groove 43 of the screw seat and is fastened by a screw plug 1, a fitting pair consisting of the connecting rod 2, the screw body 5, and the screw seat 4 is in clearance fit, and the screw body 5 and the screw seat 4 can still swing and rotate within a design scope under the action of an external force.

Further, in the present embodiment, after the degradable stopper 3a is added to the regular semi-spherical screw body sphere head 521, a natural state is that the upper end face 31, compressed by the connecting rod 2, of the degradable stopper 3a is higher than the plane of the bottom 42 of the U-shaped groove of the screw seat. At this moment, the connecting rod 2 clamped into the U-shaped groove 43 of the screw seat cannot be in contact with the bottom 42 of the U-shaped groove naturally. After the screw plug 1 is fastened, the surface of the stopper may be compressed to sink by the connecting rod 2, so as to be closely connected to the bottom 42 of the U-shaped groove.

In the present embodiment, after the degradable stopper 3a is added between an upper end of the screw body sphere head 52 and the connecting rod 2 and when the connecting rod 2 is pressed downward to be in contact with the degradable stopper 3a by the screw plug 1, the lower edge of the cylindrical connecting rod 2 and an upper end face 31 of the stopper 3a have a structural feature that is in linear or line-shaped arc surface contact in the axial direction of the connecting rod 2, which can constrain the screw body 5 and the screw seat 4 in a coaxial state of nearly rigid connection in the axial direction of the connecting rod 2, that is, an axial neutral position state, eliminate the swinging of the screw body 5 and the screw seat 4 in the axial direction of the connecting rod 2, so as to basically maintain the screw body and the screw seat in the neutral position state in the axial direction of the connecting rod 2 in initial surgery, and facilitate smooth implementation of opening and pressurizing operations. Meanwhile, the rotation between the screw body 5 and the screw seat 4 and a radial swinging function along the connecting rod 2 can also be maintained, which greatly facilitates adjusting an included angle of the screw seat 4 and the screw body 5 in the radial direction of the connecting rod 2 along a radial plane of the connecting rod 2 when the connecting rod 2 is difficult to be clamped into all U-shaped grooves 43 of the screw seats since screw entrance points and inner inclination angles of the pedicle screws implanted into adjacent two, particularly more than three, spines are different during the surgery, so that self-adaption can be produced when the connecting rod is installed, and the installation is more convenient.

In the present embodiment, after all operations of screw implanting, opening, pressurizing, and the like are completed, and finally screw plugs 1 of all pedicle screws are fastened, the screw body sphere head 52 and the fitting pair consisting of the connecting rod 2 and the inner spherical surface 41 of the lower end of the screw seat become interference fit due to the addition of the degradable stopper 3a, that is, after the connecting rod 2 is extruded by the screw plug 1, the pressure may stop the rotation of the screw body sphere head 52 and the swinging in all directions through the degradable stopper 3a, so that the connection between the screw body 5 and the screw seat 4 is changed from nearly rigid connection during the operations of opening and pressurizing into rigid connection. Therefore, in the end of the surgery and a period of time thereafter, the overall pedicle screw-rod system is equivalent to a static pedicle screw-rod system that achieves an effect of rigid fixation.

As time goes on, the degradable stopper 3a is degraded, thinned, and softened day by day until it disappears, and the lower edge of the connecting rod 2 and the upper end of the screw body sphere head 52 return to floating point contact, even cause a gap, or are out of contact. The extrusion force from top to bottom on the screw body sphere head 52 will be weakened until disappearing. The fitting pair consisting of the connecting rod 2, the screw body sphere head part 52, and the inner spherical surface 41 of the lower end of the screw seat recovers to original clearance fit gradually, so that the screw body 5 gradually obtains a swinging function within a preset scope relative to the screw seat 4 in the axial direction of the connecting rod 2 under the driving of an external force. The overall pedicle screw-rod system can gradually change from the static pedicle screw-rod system which achieves an effect of rigid fixation to the dynamic pedicle screw-rod system which achieves an effect of non-rigid fixation.

In the present embodiment, the stopper 3a is preferably made of a magnesium metal/polylactic acid composite material which takes magnesium metal with higher elastic modulus and higher degradation rate as an inner core and takes polylactic acid with lower elastic modulus and lower degradation rate and capable of compressed to sink to produce plastic deformation by the connecting rod 2 extruded by the screw plug 1 as a surface layer. Thus, the degradation time of the stopper can be prolonged, and the connecting rod 2 may sink to the bottom 42 of the U-shaped groove by using the plasticity of the surface 31 of the degradation stopper when the screw plug 1 is screwed in the case where the upper end face 31, compressed by the connecting rod 2, of the degradable stopper 3a is slightly, for example, 0.1 to 1 mm, higher than the bottom 42 of the U-shaped groove, which prevents the stopper 3a from being overhead after degradation and absorption. Meanwhile, it is ensured that the screw body sphere head 52 and the fitting pair consisting of the connecting rod 2 and the inner spherical surface 41 of the lower end of the screw seat become interference fit due to the addition of the degradable stopper 3a, so as to stop the rotation of the screw body sphere head 52 and the swinging in all directions. The connection between the screw body and the screw seat is converted from nearly rigid connection during the operations of opening and pressurizing into rigid connection. Therefore, in the end of the surgery and a period of time thereafter, the overall pedicle screw-rod system is equivalent to a static pedicle screw-rod system that achieves an effect of rigid fixation, so as to achieve the objective of the present disclosure.

Figure 13:
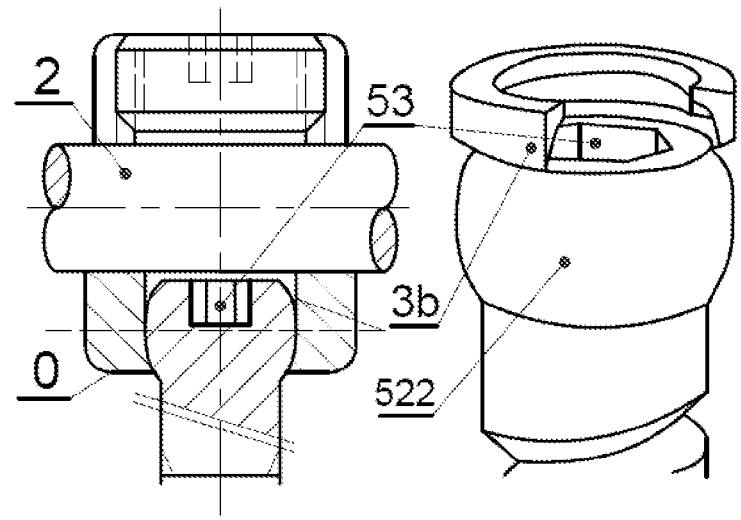
FIG. 13 is a two-dimensional diagram and an effect diagram of Embodiment 3 of the present application.

Embodiment 3, as shown in FIG. 13 and FIG. 18, is a dynamic screw that a screw body sphere head 52 is hinged to an inner spherical surface 41 of a lower end of a screw seat through a ball-socket structure in a clearance fit state. The screw body sphere head 52 is a high semi-spherical screw body sphere head 522 with a concave type screwdriver interface at a top end. A side wall of the screwdriver interface 53 forms a circle of platform with the outside diameter less than the sphere diameter at the top end of the sphere head. A degradable stopper 3b made of a hard biomaterial is added to the top end of the high semi-spherical screw body sphere head 522. A lower end face of the degradable stopper is a surface matched with the top end of the high semi-spherical sphere head and extending from the concave spherical surface of an outer ring and a platform of an inner ring. According to the shape of an upper end face 31 of the degradable stopper 3b when the screw body 5 is installed into the screw seat 4 coaxial with the screw seat 4, the degradable stopper 3b is divided into a plane type 3b-1 perpendicular to the plane of the axis of a screw body-screw seat and a concave arc 3b-2 with a concave arc surface that is perpendicular to the axis of the screw body-screw seat and is in arc surface contact with a lower edge of a connecting rod 2. Further, the degradable stopper 3b is provided with a circular hole that is perpendicular to a cross section and may be used for a screwdriver to pass through to connect the screwdriver interface 53 of the sphere head of the screw body 5. The degradable stopper 3b may be assembled in the screw seat 4 before a surgery, and is blocked by an anti-falling bulge 44 of a retaining device, which does not falls off easily.

Preferably, in the present embodiment, before the degradable stopper is added, and after the connecting rod 2 is clamped into a U-shaped groove 43 and is fastened by a screw plug 1, a fitting pair consisting of the connecting rod 2, the screw body 5, and the screw seat 4 are in clearance fit, and the screw body 5 and the screw seat 4 can still swing and rotate within a design scope under the action of an external force.

Further, in the present embodiment, after the degradable stopper 3b is added to the high semi-spherical screw body sphere head 522, a natural state is that the upper end face 31, compressed by the connecting rod, of the degradable stopper 3b is higher than the plane of the bottom 42 of the U-shaped groove of the screw seat. At this moment, the connecting rod 2 clamped into the U-shaped groove 43 of the screw seat cannot be in contact with the bottom 42 of the U-shaped groove naturally. After the screw plug 1 is fastened, the surface of the stopper 3b may be compressed to sink by the connecting rod, so as to be closely connected to the bottom 42 of the U-shaped groove.

In the present embodiment, after the degradable stopper 3b is added between an upper end of the screw body sphere head 52 and the connecting rod 2 and when the connecting rod 2 is pressed downward to be in contact with the degradable stopper 3b by the screw plug 1, the lower edge of the cylindrical connecting rod 2 and the upper end face 31 of the stopper 3b have a structural feature that is in linear or line-shaped arc surface contact in the axial direction of the connecting rod 2, which can constrain the screw body 5 and the screw seat 4 in a coaxial state of nearly rigid connection in the axial direction of the connecting rod 2, that is, an axial neutral position state, eliminate the swinging between the screw body 5 and the screw seat 4 in the axial direction of the connecting rod, so as to basically maintain the screw body and the screw seat in the neutral position state in the axial direction of the connecting rod 2 in initial surgery, and facilitate smooth implementation of opening and pressurizing operations. Meanwhile, the rotation between the screw body 5 and the screw seat 4 and a radial swinging function along the connecting rod 2 can also be maintained, which greatly facilitates adjusting an included angle of the screw seat 4 and the screw body 5 in the radial direction of the connecting rod along a radial plane of the connecting rod 2 when the connecting rod 2 is difficult to be clamped into all U-shaped grooves 43 of the screw seats since screw entrance points and inner inclination angles of the pedicle screws implanted into adjacent two, particularly more than three, spines are different during the surgery, so that self-adaption can be produced when the connecting rod 2 is installed, and the installation is more convenient.

In the present embodiment, after all operations of screw implanting, opening, pressurizing, and the like are completed, and finally screw plugs 1 of all pedicle screws are fastened, the screw body sphere head 52 and the fitting pair consisting of the connecting rod 2 and the inner spherical surface 41 of the lower end of the screw seat become interference fit due to the addition of the degradable stopper 3b, that is, after the connecting rod 2 is extruded by the screw plug 1, the pressure may stop the rotation of the screw body sphere head 52 and the swinging in all directions through the degradable stopper 3b, so that the connection between the screw body 5 and the screw seat 4 is changed from nearly rigid connection during the operations of opening and pressurizing into rigid connection. Therefore, in the end of the surgery and a period of time thereafter, the overall pedicle screw-rod system is equivalent to a static pedicle screw-rod system that achieves an effect of rigid fixation.

As time goes on, the degradable stopper 3b is degraded, thinned, and softened day by day until it disappears, and the lower edge of the connecting rod 2 and the upper end of the screw body sphere head 52 return to floating point contact, even cause a gap, or are out of contact. The extrusion force from top to bottom on the screw body sphere head 52 will be weakened until disappearing. The fitting pair consisting of the connecting rod 2, the screw body sphere head part 5, and the inner spherical surface 41 of the lower end of the screw seat recovers to original clearance fit gradually, so that the screw body 5 gradually obtains a swinging function within a preset scope relative to the screw seat 4 in the axial direction of the connecting rod 2 under the driving of an external force. The overall pedicle screw-rod system can gradually change from the static pedicle screw-rod system which achieves an effect of rigid fixation to the dynamic pedicle screw-rod system which achieves an effect of non-rigid fixation.

In the present embodiment, the stopper 3b is preferably made of a magnesium metal/polylactic acid composite material which takes magnesium metal with higher elastic modulus and higher degradation rate as an inner core and takes polylactic acid with lower elastic modulus and lower degradation rate and capable of compressed to sink to produce plastic deformation by the connecting rod 2 extruded by the screw plug 1 as a surface layer. Thus, the degradation time of the stopper can be prolonged, and the connecting rod may sink to the bottom 42 of the U-shaped groove by using the plasticity of the surface of the degradation stopper 3b when the screw plug 1 is screwed in the case where the upper end face, compressed by the connecting rod, of the degradable stopper 3b is slightly, for example, 0.1 to 1 mm, higher than the bottom 42 of the U-shaped groove of the screw seat, which prevents the stopper from being overhead after degradation and absorption. Meanwhile, it is ensured that the screw body sphere head 52 and the fitting pair consisting of the connecting rod 2 and the inner spherical surface 41 of the lower end of the screw seat become interference fit due to the addition of the degradable stopper 3b, so as to stop the rotation of the screw body sphere head 52 and the swinging in all directions. The connection between the screw body 5 and the screw seat 4 is converted from nearly rigid connection during the operations of opening and pressurizing into rigid connection. Therefore, in the end of the surgery and a period of time thereafter, the overall pedicle screw-rod system is equivalent to a static pedicle screw-rod system that achieves an effect of rigid fixation, so as to achieve the objective of the present disclosure.

Figure 14:
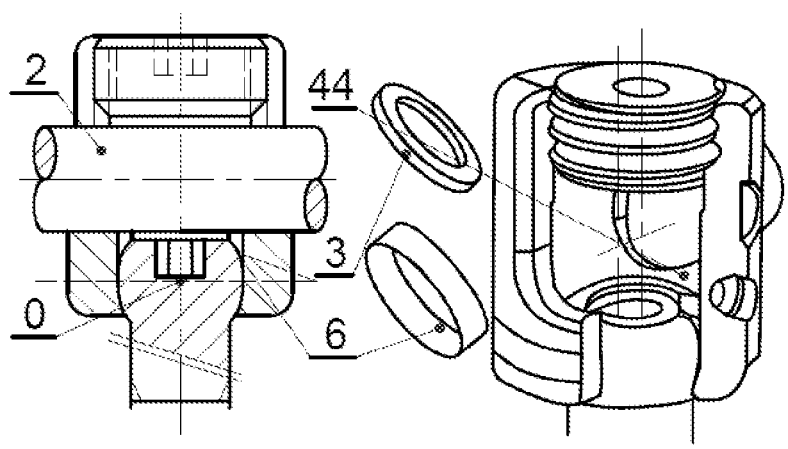
FIG. 14 is a two-dimensional diagram and an effect schematic diagram of Embodiment 4 of the present application.

Embodiment 4, as shown in FIG. 14 and FIG. 18, is a dynamic screw that a screw body sphere head 52 is hinged to an inner spherical surface 41 of a lower end of a screw seat through a ball-socket structure in a clearance fit state. The screw body sphere head 52 is a high semi-spherical screw body sphere head 522 with a concave type screwdriver interface at a top end. A side wall of the screwdriver interface 53 forms a circle of platform with the outside diameter less than the sphere diameter at the top end of the sphere head. A non-degradable pressing ring 6 with a plane extending from the platform of the side wall of the screwdriver interface as an upper surface and a concave spherical surface as a lower surface is connected to the outer edge of the top end of the sphere head 52 in a sleeving manner, and a degradable stopper 3*c* made of a degradable hard biomaterial is added to the top end of the pressing ring 6 of the high semi-spherical screw body sphere head 522. A lower surface of the degradable stopper 3*c* is in a plane and is tiled on the pressing ring 6. According to the shape of the upper end face 31 of the degradable stopper 3*c* when the screw body 5 is installed into the screw seat 4 coaxial with the screw seat 4, the degradable stopper 3*c* is divided into a plane type 3*c*-1 perpendicular to the plane of the axis of a screw body-screw seat and a concave arc 3*c*-2 with a concave arc surface that is perpendicular to the axis of the screw body-screw seat and is in arc surface contact with a lower edge of a connecting rod 2. Further, the degradable stopper 3*c* is provided with a circular hole that is perpendicular to a cross section and may be used for a screwdriver to pass through to connect a screwdriver interface 53 of the sphere head of a screw body 5. The stopper 3*c* may be assembled in the screw seat 4 before a surgery, and is blocked by an anti-falling bulge 44 of a retaining device, which does not falls off easily.

The rest structures and functions of Embodiment 4 are the same as those of Embodiment 3.

Embodiment 5, as shown in FIG. 15, FIG. 16, FIG. 17, and FIG. 18, for a dynamic screw that a sphere head at an upper end of a screw body 5 is hinged to a lower end of the screw seat 4 through a ball-socket structure in a clearance fit state, a conventional concave type screwdriver interface at the top end of the screw body 5 may also be changed into a convex type screwdriver interface. The convex type screwdriver interface 53 is in a cylindrical shape with a hexagonal or quadrangular or elliptical cross section. A boss 54 containing the axis of the screw body is processed at an upper end of the convex type screwdriver interface 53, and the spherical shape of the top end of the boss 54 is kept as the same spherical shape of the sphere head 52 of the screw body with an overlapped sphere center, so that the sphere head forms a completely spherical screw body sphere head 523. The spherical surface of the top end of the boss 54 is not higher than the bottom surface 42 of the U-shaped groove of the screw seat. A degradable stopper 3*d* made of a hard biomaterial is added to the top end of the completely spherical screw body sphere head 523. The degradable stopper 3*d* wraps and is attached to the outer edge of the boss 54, but does not cover the spherical surface of the top end of the boss 54. According to the shape of the upper end face 31 of the degradable stopper 3*d* when the screw body 5 is installed into the screw seat 4 coaxial with the screw seat 4, the degradable stopper 3*d* is divided into a plane type 3*d*-1 perpendicular to the plane of the axis of the screw body-screw seat and a concave arc 3*d*-2 with a concave arc surface that is perpendicular to the axis of the screw body-screw seat and is in arc surface contact with a lower edge of a connecting rod 2.

In the present embodiment, before the degradable stopper 3*d* is added and after the screw plug 1 is screwed to complete the fixation of the pedicle screw-rod system, the bottom end of the cylindrical connecting rod 2 and the spherical surface of the top end of the boss 54 of the screw body sphere head are in a point contact or non-contact state, so that there is no force to limit the swinging between the screw body 5 and the screw seat 4 under the driving of the external force. Therefore, the pedicle screw becomes a dynamic screw with a swinging function between the screw body 5 and the screw seat 4.

In order to realize a gradually changing function of the present disclosure, the plane or the concave arc surface of the upper end face 31 of the stopper 3*d* is tangent to the spherical surface at the top end of the boss 54 of the screw body sphere head or is slightly, 0.1 to 1 mm, higher than the spherical surface of the top end of the boss 54 of the screw body. The lower end surface of the stopper 3*d* may be overhead, and may also be supported on an extending surface of the boss 54 of the sphere head of the screw body and the screwdriver interface. In order to facilitate the operation of the screwdriver, the outside diameter of the lantern ring-shaped stopper is not greater than the minimum diameter of the screwdriver interface.

After the degradable stopper 3*d* is installed at an upper end of the completely spherical screw body sphere head 523 in a sleeving manner and the connecting rod 2 is pressed downward to be in contact with the degradable stopper 3*d* by the screw plug 1, the lower edge of the cylindrical connecting rod 2 and an upper end face 31 of the lantern ring-shaped stopper 3*d* have a structural feature that is in linear or line-shaped arc surface contact in the axial direction of the connecting rod 2, which can constrain the screw body 5 and the screw seat 4 in a coaxial state of nearly rigid connection in the axial direction of the connecting rod 2, that is, an axial neutral position state, and eliminate the swinging between the screw body 5 and the screw seat 4 in the axial direction of the connecting rod 2, so as to basically maintain the screw body and the screw seat in the neutral position state in the axial direction of the connecting rod 2 in initial surgery, and facilitate smooth implementation of opening and pressurizing operations. Meanwhile, the rotation between the screw body 5 and the screw seat 4 and a radial swinging function along the connecting rod 2 can also be maintained, which greatly facilitates adjusting an included angle of the screw seat 4 and the screw body 5 in the radial direction of the connecting rod 2 along a radial plane of the connecting rod 2 when the connecting rod 2 is difficult to be clamped into all U-shaped grooves 43 of the screw seats since screw entrance points and inner inclination angles of the pedicle screws implanted into adjacent two, particularly more than three, spines are different during the surgery, so that self-adaption can be produced when the connecting rod 2 is installed, and the installation is more convenient.

In the present embodiment, after all operations of screw implanting, opening, pressurizing, and the like are completed, and finally screw plugs 1 of all pedicle screws are fastened, the plane or the concave arc surface at the top end of the stopper 3*d* is tangent to the spherical surface at the top end of the boss 54 of the screw body sphere head, the constraint force between the screw body 5 and the screw seat 4 in the axial direction of the connecting rod 2 can be strengthened, but it is not enough to limit the constraint force between the screw body and the screw seat in the radial direction of the connecting rod 2. The situation is applied to non-fusion fixation of a spine, which lightens axial burden of the spine and maintains moderate intervertebral activity. Thereafter, as time goes on, the degradable stopper 3*d* is degraded, thinned, and softened day by day until it disappears, and the lower edge of the connecting rod 2 and the upper end of the screw body sphere head 52 return to point contact, even cause a gap, or are out of contact. The extrusion force from top to bottom on the screw body sphere head 52 will be weakened until disappearing. The fitting pair consisting of the connecting rod 2, the screw body sphere head part 52, and the inner spherical surface 41 of the lower end of the screw seat recovers to original clearance fit gradually, so that the screw body 5 gradually obtains a swinging function within a preset scope relative to the screw seat 4 in the axial direction of the connecting rod 2 under the driving of an external force. The overall pedicle screw-rod system can gradually change from the static pedicle screw-rod system which achieves an effect of rigid fixation to the dynamic pedicle screw-rod system which achieves an effect of non-rigid fixation.

Another design case is that: in the present embodiment, after all operations of screw implanting, opening, pressurizing, and the like are completed, and finally screw plugs 1 of all pedicle screws are fastened, the plane or the concave arc surface at the top end of the lantern ring-shaped stopper is slightly, 0.1 to 1 mm, higher than the spherical surface at the top end of the boss 54 of the screw body sphere head, the screw body sphere head 52 and the fitting pair consisting of the connecting rod 2 and the inner spherical surface 41 of the lower end of the screw seat 4 become interference fit by the addition of a lantern ring-shaped gasket made of a magnesium-polylactic acid composite material, that is, after the connecting rod 2 is extruded by the screw plug 1, the pressure may stop the rotation of the screw body 5 and the swinging in all directions through the degradable stopper 3, so that the connection between the screw body 5 and the screw seat 4 is changed from nearly rigid connection during the operations of opening and pressurizing into rigid connection. Therefore, in the end of the surgery and a period of time thereafter, the overall pedicle screw-rod system is equivalent to a static pedicle screw-rod system that achieves an effect of rigid fixation. After that, as time goes on, the degradable stopper 3*d* is degraded, thinned, and softened day by day until it disappears, and the lower edge of the connecting rod 2 and the upper end of the screw body sphere head 52 return to point contact, even cause a gap, or are out of contact. In addition, the extrusion force from top to bottom on the screw body sphere head 52 will be weakened until disappearing. The fitting pair consisting of the connecting rod 2, the screw body sphere head part 52, and the inner spherical surface 41 of the lower end of the screw seat recovers to original clearance fit gradually, so that the screw body 5 gradually obtains a swinging function within a preset scope relative to the screw seat 4 in the axial direction of the connecting rod 2 under the driving of an external force. The overall pedicle screw-rod system can gradually change from the static pedicle screw-rod system which achieves an effect of rigid fixation to the dynamic pedicle screw-rod system which achieves an effect of non-rigid fixation.

In order to further describe the present disclosure, the action principle of the present disclosure will now be described in detail in combination with Embodiment 5.

Figure 15:
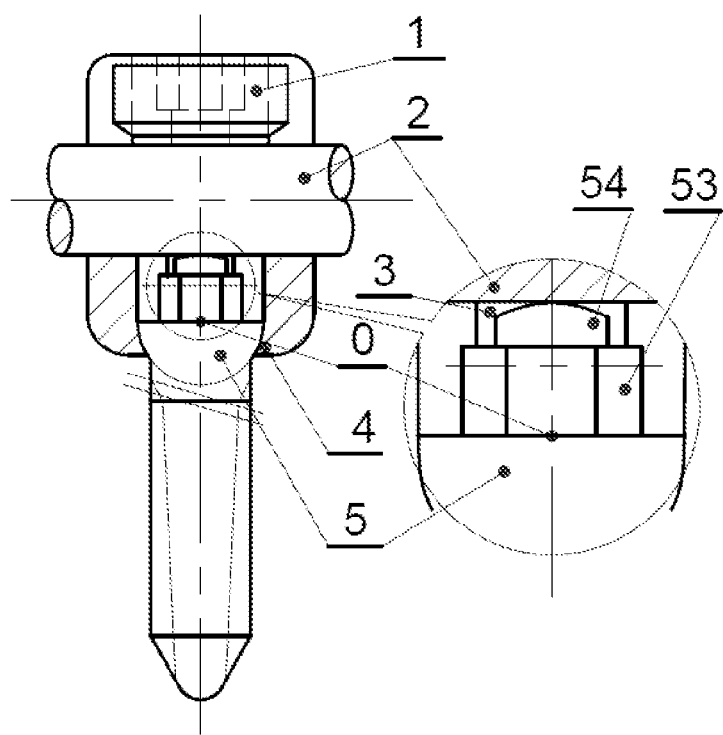
FIG. 15 is a two-dimensional diagram and a locally enlarged diagram of Embodiment 5 of the present application.
Figure 16:
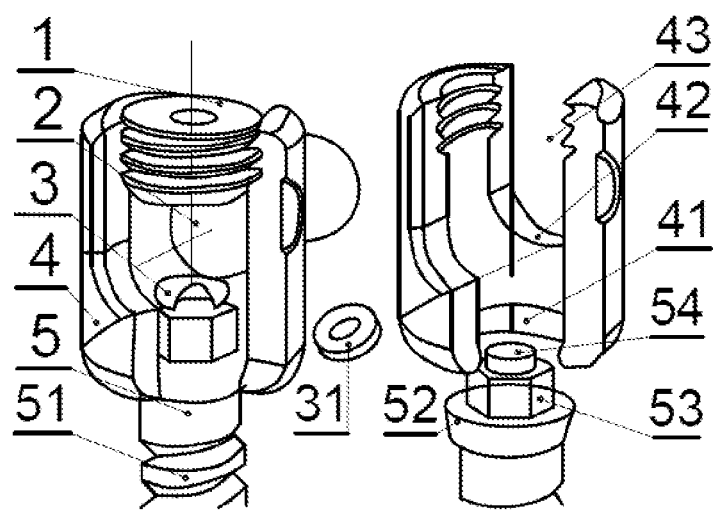
FIG. 16 is an effect and exploded decomposition schematic diagram of Embodiment 5 of the present application.

FIG. 15 is a two-dimensional diagram and a locally enlarged diagram of Embodiment 5 of the present application. FIG. 16 is a decomposition effect drawing of Embodiment 5 of the present application. It can be seen from the drawings that the screw plug 1, the connecting rod 2, and the screw seat 4 basically continue to use components of a conventional pedicle screw. The technical measure adopted in the present application is to slightly improve the feature of the head of the screw body 5 to match and place a newly added stopper 3*d* made of a hard degradable biomaterial, so as to place the stopper 3*d* on the boss 54 of the sphere head of the screw body in a sleeving manner.

Figure 17:
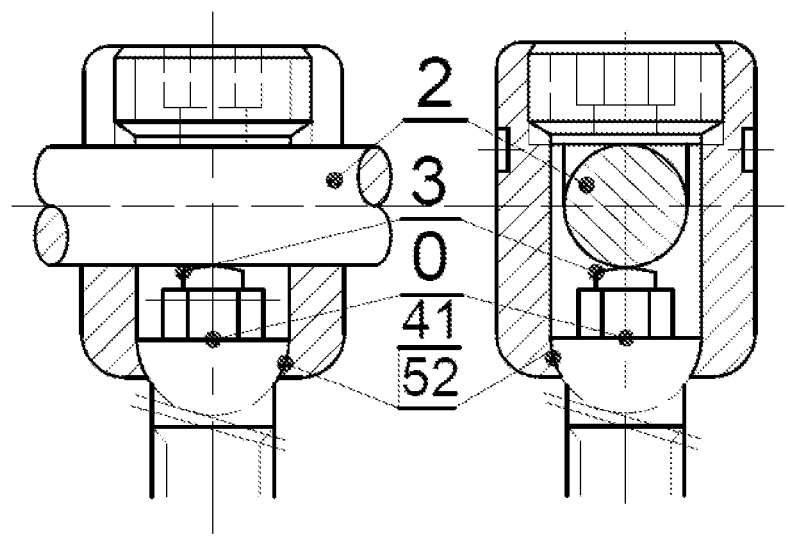
FIG. 17 is a two-dimensional schematic diagram of an axial and radial swing difference of Embodiment 5 of the present application.

FIG. 17 is a schematic diagram of a switching function of Embodiment 5 of the present disclosure. It can be seen from FIG. 17 that the upper end face 31 of the stopper 3*d*-1, the highest point of the boss 54 of the sphere head of the screw body, and the bottom 42 of the U-shaped groove of the screw seat are located on the same plane, and when the cylindrical connecting rod 2 is compressed by the screw plug 1 to be supported on the U-shaped groove 43 of the screw seat, the lower edge of the connecting rod 2 must be in linear coincidence with the stopper 3*d*-1 in the axial direction of the connecting rod 2, and is overlapped with the plane at the bottom 42 of the U-shaped groove of the screw seat. Under the limitation of the stopper 3*d*-1, the screw body 5 cannot swing around a sphere center O in the axial direction of the connecting rod 2 relative to the screw seat 4. The overall pedicle screw is in a relatively fixed state with the function of a "static screw", which is the function required at an initial stage of a surgery.

However, in a certain set period of time after the surgery, the stopper 3*d*-1 arranged on the boss 54 of the sphere head of the screw body in a sleeving manner is gradually degraded, so the plane of the upper end face 31 of the stopper 3*d*-1 gradually decreases until it disappears. The screw body 5 can swing at a certain angle around the sphere center without the constraint of the plane, and the semi-spherical surface 52 at the head of the screw body 5 and a top curved surface of the boss 54 of the top end are the same spherical surface with an overlapped sphere center. Under joint constraint of the inner spherical surface 41 at the lower end of the screw seat and the outer surface of the connecting rod 2, the swinging will not produce movement. The swinging amplitude is progressive along with gradual degradation of the degradable stopper 3*d*-1, which achieves a medical effect that is expected clinically.

It can be seen from the exploded view of FIG. 16 that Embodiment 5 of the present application only modifies the head of the traditional screw body (also called "sphere head screw"), and changes the conventional concave type screwdriver interface 53 into a convex type hexagonal cylindrical screwdriver interface 53. In addition, a boss 54 is processed at the upper end of the hexagonal cylindrical screwdriver interface 53, and the top surface of the boss 54 is still kept as the original spherical surface, so that the screw body 5 is in point contact with the connecting rod 2, which facilitates the swinging between the screw body 5 and the screw seat 4. After the stopper 3*d*-1 is connected to the boss 54 in a sleeving manner, the screw body 5 and the connecting rod 2 change into linear contact, so that the swinging of the screw body 5 in the plane where the axis of the connecting rod 2 is located.

FIG. 17 shows two two-dimensional diagrams, and a mutual relationship thereof is a relationship between a front view and a side view. A left side and a right side of a center line of each drawing are respectively a state with the existence of the stopper 3*d*-1 and the state after the stopper 3*d*-1 is degraded.

It can be seen from the left side of the center line of the two-dimensional diagram of the left side of FIG. 17, the connecting rod 2 is pressed against the upper end face 31 of the stopper 3*d*-1, so that the screw body 5 cannot swing around the point O in the plane where the axis of the connecting rod 2 is located. It can be seen from the left side of the center line of the side view on the right side of FIG. 17, although the connecting rod 2 is also pressed against the upper end face 31 of the stopper 3*d*-1, the screw body 5 can still adjust and swing at a certain angle in the radial plane of the connecting rod 2, which greatly facilitates adjusting an included angle of the screw seat 4 and the screw body 5 along a radial plane of the connecting rod 2 when the connecting rod 2 is difficult to be clamped into all U-shaped grooves 43 of the screw seats since screw entrance points and inner inclination angles of the pedicle screws implanted into adjacent two, particularly more than three, spines are different during the surgery, so as to adapt to the clamping of the connecting rod 2. Both right sides of the center lines of the two views in FIG. 7 show the situation that the stopper 3*d*-1 disappears due to degradation, so that the screw body 5 can swing around the sphere center O and recover to the function of the "dynamic screw".

FIG. 18 shows features of four different embodiments configured by the stopper 3 disclosed by the present application corresponding to different types of "dynamic screw". The stopper with a concave arc surface serving as an upper end face is located at an upper layer of a picture, and is expressed with suffix -2. The stopper with a plane as the upper end face is located at a middle layer of the picture, and is expressed with suffix -1. Three embodiments of the screw body sphere head 52 matched and adapted to the stoppers are located at a lower layer of the picture. The embodiments shown above are only a few listed in the present application. Therefore, any modification, equivalent replacement, improvement, and the like made by using the contents of the description and drawings of the description of the present disclosure shall be included in the scope of protection of the present disclosure.

It is to be noted that, herein, terms "include" and "contain" or any other variants thereof are intended to cover nonexclusive inclusions, so that a process, a method, or an apparatus including a series of elements not only includes those elements, but also includes other elements which are not clearly listed or further includes intrinsic elements of the process, the method or the apparatus. In the absence of more restrictions, elements defined by the phrase "include a reference structure" do not exclude the existence of additional identical elements in the process, method, article, or device that includes the elements.

Although the embodiments of the present disclosure have been shown and described, those of ordinary skill in the art can understand that a variety of changes, modifications, substitutions and variants can be made to these embodiments without departing from the principle and purpose of the present disclosure, and the scope of the present disclosure is defined by the claims and their equivalents.

What is claimed is:

1. A pedicle screw-rod system capable of gradually changing from rigid fixation to non-rigid fixation, pedicle screw-rod system comprising: a pedicle screw; a connecting rod; and a screw plug;
   wherein the connecting rod is used for connecting in series the pedicle screw, the pedicle screw is adapted to be fixed to adjacent vertebrae on the same side of a spine, and the screw plug is used for locking the connecting rod on the pedicle screw intersecting therewith;
   at least one of the pedicle screw or the connecting rod is connected by flexible connecting parts, and the flexible connecting parts are also connected to a degradable stopper for preventing flexible connecting parts from swinging each other; and with gradual degradation of the degradable stopper, a fixation manner of the pedicle screw-rod system will be gradually converted from initial rigid fixation into non-rigid fixation.

2. The pedicle screw-rod system according to claim 1, wherein the flexible connecting part comprises a spring; and one end of the spring is connected to a screw seat, and the other end of the spring is connected to a screw body.

3. The pedicle screw-rod system according to claim 2, wherein external threads matched with threads in an inner wall of the spring in shape are formed in an outer surface of the degradable stopper; a first screwdriver interface is formed in the center of an upper end face of a first degradable stopper; and a bulge matched with a blind hole in an upper end of the screw body is formed in the center of a lower end of the degradable stopper in an axial direction.

4. The pedicle screw-rod system according to claim 2, wherein the screw seat is of a cylinder structure with a thin upper part and a thick lower part, a high upper part and a low lower part, and a circular arc transition surface; a radius of the circular arc transition surface of an outer edge of the screw seat is consistent with a radius of the connecting rod; a second screwdriver interface is formed in an upper end face of the screw seat; the second screwdriver interface comprises notches that are symmetrically formed in a peripheral wall of the screw seat about an axis; and an axial through hole matched with the outer part of the flexible connecting part in size and shape is formed in a lower part of an inner cavity of the screw seat.

5. The pedicle screw-rod system according to claim 4, further comprising a hook frame used for fastening the connecting rod, wherein the hook frame comprises a lantern ring and a barb-shaped rod pressing arm which is arranged on a side of the lantern ring and extends outwards; the lantern ring is connected to an outer edge of the screw seat in a sleeving manner; a lower edge of the rod pressing arm is a rod pressing arc surface with the radius consistent with that of the connecting rod; a lower edge of the rod pressing arm is a rod pressing frame formed with the rod pressing arm; after the hook frame is connected to the screw seat in a sleeving manner, a semicircular arc surface of the rod pressing frame and a circular arc transition surface of the outer edge of the screw seat form a tunnel for accommodating the connecting rod together, so that the connecting rod is located on the outer side of the screw seat.

6. The pedicle screw-rod system according to claim 5, wherein a lantern ring inner cavity of the hook frame is matched with an outer edge of the screw seat; the lantern ring and the rod pressing arm are of an integrated structure; and the rod pressing arc surface intersects with the lantern ring inner cavity, so as to from a lantern ring gap.

7. The pedicle screw-rod system according to claim 2, wherein there is no screw head at an upper end of the screw body; the upper end face is a plane; a circular blind hole is formed in a center of the upper end face in an axial direction; and an adaptation groove matched with the lower end of the spring in shape is also formed in the edge of the upper end face of the screw body.

8. The pedicle screw-rod system according to claim 2, wherein an upper end of the spring is screwed with a lower end of the screw seat and is permanently and mechanically fixed; and a lower end of the spring is screwed with an upper end of the screw body and is permanently and mechanically fixed.

9. The pedicle screw-rod system according to claim 2, wherein the screw plug comprises an upper cover; a third screwdriver interface is formed in the center of the upper cover; and external threads matched with internal threads at an upper end of the screw seat are formed in a lower part of the screw plug.

10. The pedicle screw-rod system according to claim 1, wherein the connecting rod comprises one section or a plurality of sections of flexible bodies that are distributed at intervals, rigid rods connected to two ends of the flexible bodies, and degradable stoppers bridged on the rigid rods at two ends of the flexible section to limit the bending of the flexible section; and the degradable stoppers may be configured to be gradually degraded, softened, and thinned in a human body until disappearing, and the connecting rod will gradually obtain the preset flexibility.

11. The pedicle screw-rod system according to claim 10, wherein the flexible body comprises a cylindrical spring; and the outside diameter of the cylindrical spring is less than or equal to that of the rigid rods.

12. The pedicle screw-rod system according to claim 11, wherein an end face of the rigid rod is provided with a concave structure or a screw core-shaped structure matched with an outer surface of the cylindrical spring; and the cylindrical spring is fixedly connected to the rigid rod through the concave structure or the screw core-shaped structure.

13. The pedicle screw-rod system according to claim 10, wherein the degradable stoppers are of tubular structures, and are connected to the flexible section of the connecting rod and the peripheries of the adjacent rigid rods at both ends thereof in a sleeving manner in a rigid state.

14. The pedicle screw-rod system according to claim 10, wherein the degradable stoppers are of inner core structures, and cylindrical springs extend out from both ends after the degradable stoppers are inserted or screwed into the cylindrical springs; and blind holes matched with the cylindrical springs extended out from the degradable stoppers are also formed in end faces of the rigid rods in an axial direction.

15. The pedicle screw-rod system according to claim 14, wherein external threads matched with an inner cavity of the cylindrical spring are formed in the middle section of the degradable stopper, and external threads matched with threaded blind holes in the end faces of the rigid rod are formed in both ends.

16. The pedicle screw-rod system according to claim 1, wherein the degradable stoppers may be manufactured by a degradable biomaterial, and is made of a magnesium metal/polylactic acid composite material which takes a magnesium metal with higher elastic modulus and higher degradation rate as an inner core and takes polylactic acid with lower elastic modulus and lower degradation rate as a surface layer.

17. The pedicle screw-rod system according to claim 1, wherein rigid pieces and the flexible connecting parts of the pedicle screw or the connecting rod are integrally manufactured in an additive manufacturing manner.

18. The pedicle screw-rod system according to claim 1, wherein a sphere head is arranged at an upper end of the screw body; the sphere head at the upper end of the screw body may also be hinged to a lower end of the screw seat in a clearance fit state; and the screw body and the screw seat can swing and rotate under the action of an external force.

19. The pedicle screw-rod system according to claim 18, wherein after the screw plug is fastened, the connection between the screw body and the screw seat may also be converted into rigid connection by making a fitting pair consisting of the connecting rod, the degradable stopper, the sphere head of the screw body, and the lower end of the screw seat in interference fit; and as the degradable stopper is gradually degraded, thinned, and softened until disappearing, the original clearance fit of the fitting pair consisting of the connecting rod, the sphere head of the screw body, and the lower end of the screw seat gradually recovers.

20. The pedicle screw-rod system according to claim 18, wherein the upper end of the screw seat is provided with a U-shaped groove and is provided with internal threads matched with the screw plug; the whole body, except the two ends, of the connecting rod is cylindrical; and before the degradable stopper is added, the highest point of a top end of the sphere head is not higher than the plane of a connecting line of bottoms of the U-shaped grooves on both sides.

21. The pedicle screw-rod system according to claim 20, wherein when the screw body is installed into the screw seat coaxially with the screw seat, the upper end face of the degradable stopper is a plane perpendicular to an axis of the screw body-screw seat or a concave arc surface that is provided with an axis perpendicular to the screw body-screw seat and is in arc surface contact with the lower edge of the connecting rod.

22. The pedicle screw-rod system according to claim 20, wherein the sphere head of the upper end of the screw body is a semi-sphere with a concave type screwdriver interface in a top end, or a complete sphere with a convex screwdriver interface in the top end; and after the degradable stopper is added to the upper end of the sphere head of the screw body, the lower edge of the connecting rod and the upper end face of the stopper have a structural feature that is in linear or line-shaped arc surface contact in an axial direction of the connecting rod.

23. The pedicle screw-rod system according to claim 20, wherein after the degradable stopper is added on the upper end of the sphere head of the screw body, a natural state is that the upper end face, compressed by the connecting rod, of the degradable stopper is higher than the plane of the bottom of the U-shaped groove of the screw seat; at this moment, the connecting rod clamped into the U-shaped groove of the screw seat cannot be in contact with the bottom of the U-shaped groove naturally; and the surface of the stopper may be compressed to sink by the connecting rod, so as to be closely connected to the bottom of the U-shaped groove.

24. The pedicle screw-rod system according to claim 20, wherein the sphere head of the upper end of the screw body is a regular semi-sphere with a concave type screwdriver interface in a top end; a side wall of the screwdriver interface forms a circle of platform at a top end of the sphere head; the degradable stopper is provided with a through hole for a screwdriver to penetrate through along an axis; and the lower end face of the degradable stopper is in a plane shape adapted to the platform.

25. The pedicle screw-rod system according to claim 20, wherein the sphere head of the upper end of the screw body is a high semi-sphere with a concave type screwdriver interface in a top end; the side wall of the screwdriver interface forms a circle of platform with the outside diameter less than the sphere diameter at the top end of the sphere head; the degradable stopper is provided with a through hole for a screwdriver to penetrate through along the axis; and a lower end face of the degradable stopper is a plane that is matched with the top end of the high semi-spherical sphere head and extends from the concave spherical surface of an outer ring and a platform of an inner ring.

26. The pedicle screw-rod system according to claim 25, wherein the sphere head of the upper end of the screw body is a high semi-sphere with a concave type screwdriver interface in a top end; an outer edge of a top end of the sphere head is connected with a pressing ring which is non-degradable with a plane serving as an upper surface and a concave spherical surface serving as a lower surface; and the degradable stopper is provided with a through hole for the screwdriver to penetrate through along the axis; and the degradable stopper is tiled on the pressing ring.

27. The pedicle screw-rod system according to claim 20, wherein a screwdriver interface at a top end of the sphere head of the screw body is in a cylindrical convex type with a hexagonal or quadrangular or elliptical cross section; a boss containing the axis of the screw body is processed at a upper end of the screwdriver interface which is in convex type; the spherical shape of the top end of the boss is kept as the same spherical surface of the sphere head of the screw body with an overlapped sphere center; the degradable stopper wraps and is attached to the outer edge of the boss, but does not cover the spherical surface of the top end of the boss; the spherical surface of the top end of the boss is not higher than the bottom surface of the U-shaped groove of the screw seat; and the outside diameter of the degradable stopper is not greater than the minimum diameter of the screwdriver interface.

* * * * *